(12) United States Patent
Hintzer et al.

(10) Patent No.: US 7,659,333 B2
(45) Date of Patent: Feb. 9, 2010

(54) FLUORINATED SURFACTANTS FOR USE IN MAKING A FLUOROPOLYMER

(75) Inventors: Klaus Hintzer, Kastl (DE); Michael Jürgens, Neuoetting (DE); Harald Kaspar, Burgkirchen (DE); Herbert Königsmann, Burgkirchen (DE); Kai Helmut Lochhaas, Neuoetting (DE); Andreas R. Maurer, Langenneufnach (DE); Tilman C. Zipplies, Burghausen (DE); Richard M. Flynn, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/562,277

(22) Filed: Nov. 21, 2006

(65) Prior Publication Data

US 2007/0117914 A1    May 24, 2007

(30) Foreign Application Priority Data

Nov. 24, 2005  (GB)  ................................ 0523853.0

(51) Int. Cl.
C08K 5/41 (2006.01)
(52) U.S. Cl. ........................ 524/156; 524/284; 524/544; 524/545; 524/546; 524/805; 526/242; 554/220; 554/225; 562/45; 562/76
(58) Field of Classification Search ................. 526/242; 521/27
See application file for complete search history.

(56) References Cited

U.S. PATENT DOCUMENTS

| | | |
|---|---|---|
| 2,713,593 A | 7/1955 | Brice et al. |
| 3,037,953 A | 6/1962 | Marks et al. |
| 3,142,665 A | 7/1964 | Cardinal et al. |
| 3,179,614 A | 4/1965 | Edwards |
| 3,260,691 A | 7/1966 | Lavin et al. |
| 3,271,341 A | 9/1966 | Garrison |
| 3,315,201 A | 4/1967 | Werme |
| 3,345,317 A | 10/1967 | Hoashi |
| 3,391,099 A | 7/1968 | Punderson |
| 3,451,908 A | 6/1969 | Sianesi et al. |
| 3,489,595 A | 1/1970 | Brown, Jr. |
| 3,555,100 A | 1/1971 | Garth et al. |
| 3,635,926 A | 1/1972 | Gresham |
| 3,642,742 A | 2/1972 | Carlson |
| 3,721,696 A | 3/1973 | Sianesi et al. |
| 3,790,403 A | 2/1974 | Ribbans, III |
| 3,855,191 A | 12/1974 | Doughty, Jr. et al. |
| 3,882,153 A | 5/1975 | Seki et al. |
| 3,981,945 A | 9/1976 | Attwood et al. |
| 4,016,345 A | 4/1977 | Holmes |
| 4,025,709 A | 5/1977 | Blaise et al. |
| 4,049,863 A | 9/1977 | Vassiliou |
| 4,123,401 A | 10/1978 | Berghmans et al. |
| 4,131,711 A | 12/1978 | Attwood |
| 4,252,859 A | 2/1981 | Concannon et al. |
| 4,262,101 A | 4/1981 | Hartwimmer et al. |
| 4,282,162 A | 8/1981 | Kuhls |
| 4,287,112 A | 9/1981 | Berghmans |
| 4,292,402 A | 9/1981 | Pollet et al. |
| 4,342,825 A | 8/1982 | Van Poucke et al. |
| 4,353,950 A | 10/1982 | Vassiliou |
| 4,369,266 A | 1/1983 | Kuhls et al. |
| 4,380,618 A | 4/1983 | Khan et al. |
| 4,381,384 A | 4/1983 | Khan |
| 4,391,940 A | 7/1983 | Kuhls et al. |
| 4,425,448 A | 1/1984 | Concannon et al. |
| 4,439,385 A | 3/1984 | Kuhls et al. |
| 4,544,458 A | 10/1985 | Grot et al. |
| 4,548,986 A | 10/1985 | Suzuki et al. |
| 4,552,925 A | 11/1985 | Nakagawa et al. |
| 4,588,796 A | 5/1986 | Wheland |
| 4,618,641 A | 10/1986 | Hengel |
| 4,621,116 A | 11/1986 | Morgan |
| 4,623,487 A | 11/1986 | Cope |
| 4,766,190 A | 8/1988 | Morita et al. |
| 4,789,717 A | 12/1988 | Giannetti et al. |
| 4,832,879 A | 5/1989 | Hamprecht |
| 4,861,845 A | 8/1989 | Slocum et al. |
| 4,864,006 A | 9/1989 | Giannetti et al. |

(Continued)

FOREIGN PATENT DOCUMENTS

CA          235138          6/2000

(Continued)

OTHER PUBLICATIONS

Machine translation of Haniyu, JP2003043625A.*

(Continued)

*Primary Examiner*—Marc S Zimmer
*Assistant Examiner*—Nicole M Buie
(74) *Attorney, Agent, or Firm*—Dena M. Enrich; Brian E. Szymanski

(57) ABSTRACT

The present invention provides a fluorinated surfactant having the general formula:

$$[R_f-(O)_t-CQH-CF_2-O]_n-R-G \qquad (I)$$

wherein $R_f$ represents a partially or fully fluorinated aliphatic group optionally interrupted with one or more oxygen atoms, Q is $CF_3$ or F, R is an aliphatic or aromatic hydrocarbon group, G represents a carboxylic or sulphonic acid or salt thereof, t is 0 or 1 and n is 1, 2 or 3. The surfactant is particularly useful in polymerizing fluorinated monomers in an aqueous emulsion polymerization.

16 Claims, No Drawings

U.S. PATENT DOCUMENTS

| | | |
|---|---|---|
| 4,987,254 A | 1/1991 | Schwertfeger et al. |
| 5,075,397 A | 12/1991 | Tonelli et al. |
| 5,153,322 A | 10/1992 | Flynn |
| 5,160,791 A | 11/1992 | Tannenbaum |
| 5,168,107 A | 12/1992 | Tannenbaum |
| 5,182,342 A | 1/1993 | Feiring et al. |
| 5,198,491 A | 3/1993 | Honda et al. |
| 5,219,910 A | 6/1993 | Stahl et al. |
| 5,223,343 A | 6/1993 | Tannenbaum |
| 5,229,480 A | 7/1993 | Uschold |
| 5,230,961 A | 7/1993 | Tannenbaum |
| 5,272,186 A | 12/1993 | Jones |
| 5,285,002 A | 2/1994 | Grootaert |
| 5,312,935 A | 5/1994 | Mayer et al. |
| 5,442,097 A | 8/1995 | Obermeier et al. |
| 5,447,982 A | 9/1995 | Kamba et al. |
| 5,453,477 A | 9/1995 | Oxenrider et al. |
| 5,463,021 A | 10/1995 | Beyer et al. |
| 5,478,651 A | 12/1995 | Tannenbaum |
| 5,488,142 A | 1/1996 | Fall et al. |
| 5,498,680 A | 3/1996 | Abusleme et al. |
| 5,530,078 A | 6/1996 | Felix et al. |
| 5,532,310 A | 7/1996 | Grenfell et al. |
| 5,562,991 A | 10/1996 | Tannenbaum |
| 5,576,381 A | 11/1996 | Bladel et al. |
| 5,591,877 A | 1/1997 | Obermeier et al. |
| 5,608,022 A | 3/1997 | Nakayama et al. |
| 5,656,201 A | 8/1997 | Vicsa et al. |
| 5,663,255 A | 9/1997 | Anolick et al. |
| 5,667,846 A | 9/1997 | Thomas |
| 5,688,884 A | 11/1997 | Baker et al. |
| 5,700,859 A | 12/1997 | Ogura et al. |
| 5,710,345 A | 1/1998 | Navarrini et al. |
| 5,721,053 A | 2/1998 | Thomas |
| 5,763,552 A | 6/1998 | Feiring et al. |
| 5,789,083 A | 8/1998 | Thomas |
| 5,789,508 A | 8/1998 | Baker et al. |
| 5,804,650 A | 9/1998 | Tsuda et al. |
| 5,895,799 A | 4/1999 | Wu et al. |
| 5,955,556 A | 9/1999 | McCarthy et al. |
| 5,959,026 A | 9/1999 | Abusleme et al. |
| 5,969,063 A | 10/1999 | Parker et al. |
| 5,990,330 A | 11/1999 | Sulzbach et al. |
| 6,013,795 A | 1/2000 | Manzara et al. |
| 6,025,307 A | 2/2000 | Chittofrati et al. |
| 6,103,843 A | 8/2000 | Abusleme et al. |
| 6,103,844 A | 8/2000 | Brothers |
| 6,126,849 A | 10/2000 | Yamana et al. |
| 6,136,893 A | 10/2000 | Yamashita et al. |
| 6,153,688 A | 11/2000 | Miura et al. |
| 6,218,464 B1 | 4/2001 | Parker et al. |
| 6,245,923 B1 | 6/2001 | Sulzbach et al. |
| 6,255,384 B1 | 7/2001 | McCarthy et al. |
| 6,255,536 B1 | 7/2001 | Worm et al. |
| 6,267,865 B1 | 7/2001 | Polson et al. |
| 6,365,684 B1 | 4/2002 | McCarthy et al. |
| 6,391,182 B2 | 5/2002 | Smeltzer et al. |
| 6,395,848 B1 | 5/2002 | Morgan et al. |
| 6,410,626 B1 | 6/2002 | Wada et al. |
| 6,429,258 B1 | 8/2002 | Morgan et al. |
| 6,436,244 B1 | 8/2002 | Fuhrer et al. |
| 6,482,979 B1 | 11/2002 | Hintzer et al. |
| 6,512,063 B2 | 1/2003 | Tang |
| 6,518,442 B1 | 2/2003 | Felix et al. |
| 6,576,703 B2 | 6/2003 | Kapeliouchko et al. |
| 6,593,416 B2 | 7/2003 | Grootaert et al. |
| 6,602,068 B2 | 8/2003 | Atemboski et al. |
| 6,610,788 B1 | 8/2003 | Takakura et al. |
| 6,613,941 B1 | 9/2003 | Felix et al. |
| 6,624,268 B1 | 9/2003 | Maekawa et al. |
| 6,632,508 B1 | 10/2003 | Pellerite et al. |
| 6,642,307 B1 | 11/2003 | Sogabe et al. |
| 6,642,415 B1 | 11/2003 | Fuhrer et al. |
| 6,660,798 B1 | 12/2003 | Marchese et al. |
| 6,677,414 B2 | 1/2004 | Hintzer et al. |
| 6,693,152 B2 | 2/2004 | Kaspar et al. |
| 6,703,520 B2 | 3/2004 | Hintzer et al. |
| 6,706,193 B1 | 3/2004 | Burkard et al. |
| 6,710,123 B1 | 3/2004 | Amin-Sanayei et al. |
| 6,737,489 B2 | 5/2004 | Linert et al. |
| 6,750,304 B2 | 6/2004 | Kaspar et al. |
| 6,761,964 B2 | 7/2004 | Tannenbaum |
| 6,774,164 B2 | 8/2004 | Lyons et al. |
| 6,794,550 B2 | 9/2004 | Hintzer et al. |
| 6,815,040 B2 | 11/2004 | Pellerite et al. |
| 6,822,059 B2 | 11/2004 | Buckanin et al. |
| 6,825,250 B2 | 11/2004 | Epsch et al. |
| 6,833,403 B1 | 12/2004 | Baldel et al. |
| 6,846,570 B2 | 1/2005 | Leech et al. |
| 6,861,466 B2 | 3/2005 | Dadalas et al. |
| 6,861,490 B2 | 3/2005 | Kaspar et al. |
| 6,869,997 B2 | 3/2005 | Wille et al. |
| 6,878,772 B2 | 4/2005 | Visca et al. |
| 6,956,078 B2 | 10/2005 | Cavanaugh et al. |
| 6,972,094 B2 | 12/2005 | Ichida et al. |
| 7,026,036 B2 | 4/2006 | Leech et al. |
| 7,045,571 B2 | 5/2006 | Tan et al. |
| 7,064,170 B2 | 6/2006 | Kaspar et al. |
| 7,074,862 B2 | 7/2006 | Kaspar et al. |
| 7,122,608 B1 | 10/2006 | Brinati et al. |
| 7,125,941 B2 | 10/2006 | Kaulbach et al. |
| 7,126,016 B2 | 10/2006 | Fu et al. |
| 7,141,620 B2 | 11/2006 | Hoshikawa et al. |
| 2002/0198345 A1 | 12/2002 | Grootaert et al. |
| 2003/0125421 A1 | 7/2003 | Bladel et al. |
| 2003/0181572 A1* | 9/2003 | Tan et al. .................... 524/502 |
| 2004/0010156 A1 | 1/2004 | Kondo et al. |
| 2004/0116742 A1 | 6/2004 | Guerra |
| 2004/0143052 A1 | 7/2004 | Epsch et al. |
| 2004/0186219 A1 | 9/2004 | Dadalas et al. |
| 2004/0242755 A1 | 12/2004 | Araki et al. |
| 2005/0043471 A1 | 2/2005 | Epsch et al. |
| 2005/0070633 A1 | 3/2005 | Epsch et al. |
| 2005/0090601 A1 | 4/2005 | Dadalas et al. |
| 2005/0090613 A1 | 4/2005 | Maruya et al. |
| 2005/0107506 A1 | 5/2005 | Kapeliouchko et al. |
| 2005/0107518 A1* | 5/2005 | Zipplies et al. ............. 524/544 |
| 2005/0113519 A1 | 5/2005 | Buckanin et al. |
| 2005/0154104 A1 | 7/2005 | Malvasi et al. |
| 2005/0228127 A1* | 10/2005 | Tatemoto et al. ........... 524/805 |
| 2006/0003168 A1 | 1/2006 | Dadalas et al. |
| 2006/0041051 A1 | 2/2006 | Nakatani et al. |
| 2006/0160947 A1 | 7/2006 | Tan et al. |
| 2006/0281946 A1 | 12/2006 | Morita et al. |
| 2007/0015864 A1* | 1/2007 | Hintzer et al. .............. 524/544 |
| 2007/0025902 A1* | 2/2007 | Hintzer et al. .......... 423/240 S |
| 2007/0082993 A1 | 4/2007 | Amin-Sanayei et al. |
| 2007/0117915 A1 | 5/2007 | Funaki et al. |
| 2007/0135558 A1 | 6/2007 | Tsuda et al. |
| 2007/0149733 A1 | 6/2007 | Otsuka et al. |
| 2007/0155891 A1 | 7/2007 | Tsuda et al. |

FOREIGN PATENT DOCUMENTS

| | | |
|---|---|---|
| DE | 3828063 | 2/1990 |
| DE | 19932771 | 1/2001 |
| DE | 19933696 | 1/2001 |
| DE | 10018853 | 10/2001 |
| EP | 0014431 | 8/1980 |
| EP | 0015481 | 9/1980 |
| EP | 0022257 | 1/1981 |
| EP | 0222945 | 11/1984 |
| EP | 0219065 A2 * | 4/1987 |
| EP | 0524585 | 1/1993 |

| | | |
|---|---|---|
| EP | 0525660 | 2/1993 |
| EP | 0612770 | 8/1994 |
| EP | 0625526 | 11/1994 |
| EP | 0632009 | 1/1995 |
| EP | 0649863 | 4/1995 |
| EP | 0712882 | 5/1996 |
| EP | 0718364 | 6/1996 |
| EP | 0739960 | 10/1996 |
| EP | 0752432 | 1/1997 |
| EP | 0816397 | 1/1998 |
| EP | 0818506 | 1/1998 |
| EP | 0890592 B1 | 1/1999 |
| EP | 0894541 | 2/1999 |
| EP | 0964009 | 12/1999 |
| EP | 0969027 | 1/2000 |
| EP | 1059333 | 12/2000 |
| EP | 1059342 | 12/2000 |
| EP | 1083441 | 3/2001 |
| EP | 1160258 | 12/2001 |
| EP | 1323677 | 7/2003 |
| EP | 1364972 | 11/2003 |
| EP | 1 334 996 | 3/2004 |
| EP | 1462461 | 9/2004 |
| EP | 1514848 | 4/2006 |
| GB | 642025 | 8/1950 |
| GB | 821353 | 10/1959 |
| GB | 966814 | 8/1964 |
| JP | 46011031 | 8/1966 |
| JP | 2000-128934 | 5/2000 |
| JP | 2002-179870 | 6/2002 |
| JP | 2002-308914 | 10/2002 |
| JP | 2002-317003 | 10/2002 |
| JP | 2003043625 A * | 2/2003 |
| JP | 2003-119204 | 4/2003 |
| JP | 2003-212919 | 7/2003 |
| JP | 2004-358397 | 12/2004 |
| JP | 2004-359870 | 12/2004 |
| JP | 2005-008775 | 1/2005 |
| JP | 2005-0105045 | 4/2005 |
| RU | 2158274 | 10/2000 |
| WO | WO 94/14904 | 7/1994 |
| WO | WO96/24622 | 8/1996 |
| WO | WO 97/17381 | 5/1997 |
| WO | WO 98/50603 | 11/1998 |
| WO | WO 00/22002 | 4/2000 |
| WO | WO 00/35971 | 6/2000 |
| WO | WO 00/52060 | 9/2000 |
| WO | WO 00/71590 | 11/2000 |
| WO | WO 01/46116 | 6/2001 |
| WO | WO 01/79332 | 10/2001 |
| WO | WO 02/14223 | 2/2002 |
| WO | WO02/20676 | 3/2002 |
| WO | WO 02/078862 | 10/2002 |
| WO | WO 02/088203 | 11/2002 |
| WO | WO 02/088206 | 11/2002 |
| WO | WO 02/088207 | 11/2002 |
| WO | WO 02/095121 | 11/2002 |
| WO | WO 03/020836 | 3/2003 |
| WO | WO 03/051988 | 6/2003 |
| WO | WO 03/087176 | 10/2003 |
| WO | WO 03/087179 | 10/2003 |
| WO | WO 2004/031141 | 4/2004 |
| WO | WO 2004/067588 | 8/2004 |
| WO | WO 2005/003075 | 1/2005 |
| WO | WO2005/042593 | 5/2005 |
| WO | WO2005/056614 | 6/2005 |
| WO | WO2005/063827 | 7/2005 |
| WO | WO2005/065800 | 7/2005 |
| WO | WO 2005/082785 | 9/2005 |
| WO | WO2005/121290 | 12/2005 |
| WO | WO2006/011533 | 2/2006 |
| WO | WO2006/020721 | 2/2006 |
| WO | WO 2007/120348 | 10/2007 |

OTHER PUBLICATIONS

England, "Catalytic Conversion of Fluoroalkyl Alkyl Ethers to Carbonyl Compounds", J. Org. Chem. 1984, vol. 49, pp. 4007-4008.*
Partial Translation of JP 2003-043625 A, [0018].*
Translation of Haniyu, JP 200343625A.*
"Guide to Protein Purification, Methods in Enzymology," Deutscher, M. vol. 182, 24. 1990. (pp. 309-317).
"High Performance Polymers for Diverse Applications," Modern Fluoropolymers. Edited by John Scheirs. John Wiley & Sons, 1997.
"Hydrogen-Ion Activity to Laminated Materials. Glass." Encyclopedia of Chemical Technology. John Wiley & Sons, vol. 13, $3^{rd}$ Ed. 1981. (p. 687).
"Immobilized Biocatalysts to Isoprene," Ullmann's Encyclopedia of Industrial Chemistry, vol. A14. 1985. (p. 439-459).
"Identification to Lignin," Encyclopedia of Polymer Science and Engineering. John Wiley & Sons, vol. 8, 1987 (p. 347).
"Nonionic Surfactants." Edited by Martin J. Schick, 1967.
"Synthesis of Perfluoroalkyl Vinyl Ether Acids and Derivatives," Perfluoroalkyl Vinyl Ether Acids. Raymond Sullivan, vol. 34, No. 6, Jun. 1969. (p. 1841).
Kokelenberg, H. and Pollet, R., "A New type fluortensides, based on the addition of nucleophiles to chlorotrifluoroethylene and hexafluoropropylene." Tenside Detergents, 1985, 22(1), pp. 22-27.
Drobny, Technology of Fluoropolymers, CRC Press LLC, 2001, p. 35.
Sudol et al., "Miniemulsion Polymerization", Emulsion Polymerization and Emulsion Polymers, John Wiley & Sons, 1997, Chapter. 20.
Candau, "Inverse Emulsion and Microemulsion Polymerization", Emulsion Polymerization and Emulusion Polymers, John Wiley & Sons, 1997, Chapter 21.
Chi et al., "A Facile Synthesis of Partly-fluorinated Ethers Using Perfluoroporpoxyethylene and Aliphatic Alcohols", Bull. Korean Chem. Soc., 1999, vol. 20, No. 2, pp. 220-222.
Ebnesajjad, "Fluoroplastics, vol. 1, Non-Melt Processable Fluoroplastics", Plastics Design Library, NY, 2000, pp. 285-295.
Ebnesajjad, "Fluoroplastics, vol. 2, Melt Processable Fluoropolymers", Plastics Design Library, NY, 2003, pp. 1-21.
ASTM D 4895-04, "Standard Specification for Polytetrafluoroethylene (PTFE) Resin Produced From Dispersion", pp. 1-14.
Storsberg, Joachim and Ritter, Helmut, "Cyclodextrins in Polymer Synthesis: A 'Green' Route to Fluorinated Polymers via Cyclodextrin Complexes in Aqueous Solution", *Macromol. Chem Phys.*, 2002, pp. 812-818.
Apostolo et al., "Microemulsion Polymerization for Producing Fluorinated Structured Materials", Macromol. Symp. 2004, 206, pp. 347-360.
Ivanova et al., "Synthesis of Alcohols from Perfluorvinyl Esters", Zh. Vses. Khim Obsh 1999, (24), pp. 656-657.
W.C. Griffin "Calculation of HLB Values of Non-Ionic Surfactants", Journal of Society of Cosmetic Chemists, vol. 5, (1954) p. 259.

* cited by examiner

FLUORINATED SURFACTANTS FOR USE IN MAKING A FLUOROPOLYMER

CROSS REFERENCE TO RELATED PATENT APPLICATION

This application claims priority to Great Britain Application No. 0523853.0, filed on Nov. 24, 2005, herein incorporated by reference in its entirety.

FIELD OF THE INVENTION

The present invention relates to fluorinated surfactants and in particular relates to fluorinated surfactants that are suitable for use in the aqueous emulsion polymerization of fluorinated monomers to produce fluoropolymers.

BACKGROUND OF THE INVENTION

Fluoropolymers, i.e. polymers having a fluorinated backbone, have been long known and have been used in a variety of applications because of several desirable properties such as heat resistance, chemical resistance, weatherability, UV-stability etc. The various fluoropolymers are for example described in "Modern Fluoropolymers", edited by John Scheirs, Wiley Science 1997. Commonly known or commercially employed fluoropolymers include polytetrafluoroethylene (PTFE), copolymers of tetrafluoroethylene (TFE) and hexafluoropropylene (HFP) (FEP polymers), perfluoroalkoxy copolymers (PFA), ethylene-tetrafluoroethylene (ETFE) copolymers, copolymers of tetrafluoroethylene, hexafluoropropylene and vinylidene fluoride (THV) and polyvinylidene fluoride polymers (PVDF). Commercially employed fluoropolymers also include fluoroelastomers and thermoplastic fluoropolymers.

Several methods are known to produce fluoropolymers. Such methods include suspension polymerization, aqueous emulsion polymerization, solution polymerization, polymerization using supercritical $CO_2$, and polymerization in the gas phase.

Currently, the most commonly employed polymerization methods include suspension polymerization and especially aqueous emulsion polymerization. The aqueous emulsion polymerization normally involves the polymerization in the presence of a fluorinated surfactant, which is generally used for the stabilization of the polymer particles formed. The suspension polymerization generally does not involve the use of surfactant but results in substantially larger polymer particles than in case of the aqueous emulsion polymerization. Thus, the polymer particles in case of suspension polymerization will quickly settle out whereas in case of dispersions obtained in emulsion polymerization generally good stability over a long period of time is obtained.

An aqueous emulsion polymerization wherein no surfactant is used has been utilized to generally produce homo- and copolymers of chlorotrifluoroethylene (CTFE).

Notwithstanding the fact that emulsifier free polymerizations are known, the aqueous emulsion polymerization process in the presence of fluorinated surfactants is still a desirable process to produce fluoropolymers because it can yield stable fluoropolymer particle dispersions in high yield and in a more environmental friendly way than for example polymerizations conducted in an organic solvent. Frequently, the emulsion polymerization process is carried out using a perfluoroalkanoic acid or salt thereof as a surfactant. These surfactants are typically used as they provide a wide variety of desirable properties such as high speed of polymerization, good copolymerization properties of fluorinated olefins with comonomers, small particle sizes of the resulting dispersion can be achieved, good polymerization yields i.e. a high amount of solids can be produced, good dispersion stability, etc. However, environmental concerns have been raised against these surfactants and moreover these surfactants are generally expensive.

It would now be desirable to find an alternative emulsion polymerization process in which the use of perfluoroalkanoic acids and salts thereof as a fluorinated surfactant can be avoided. In particular, it would be desirable to find an alternative surfactant or dispersant, in particular one that is more environmentally friendly, for example has a low toxicity and/or shows no or only little bioaccumulation. It would also be desirable that the alternative surfactant has good chemical and thermal stability enabling polymerization over a wide range of conditions of for example temperature and/or pressure. Desirably, the alternative surfactant or dispersant allows for a high polymerization rate, good dispersion stability, good yields, good copolymerization properties; no or limited telogenic effects and/or the possibility of obtaining a wide variety of particle sizes including small particle sizes. The properties of the resulting fluoropolymer should generally not be negatively influenced and preferably would be improved. Desirably, the resulting dispersions have good or excellent properties in coating applications and/or impregnation of substrates, including for example good film forming properties. It would further be desirable that the polymerization can be carried out in a convenient and cost effective way, preferably using equipment commonly used in the aqueous emulsion polymerization of fluorinated monomers. Additionally, it may be desirable to recover the alternative surfactant or dispersant from waste water streams and/or to remove or recover the surfactant from the dispersion subsequent to the polymerization. Desirably, such recovery can proceed in an easy, convenient and cost effective way.

SUMMARY OF THE INVENTION

In accordance with one aspect of the present invention, there is provided a fluorinated surfactant having the general formula:

$$[R_f\text{—}(O)_t\text{—}CQH\text{—}CF_2\text{—}O]_n\text{—}R\text{—}G \quad (I)$$

wherein $R_f$ represents a partially or fully fluorinated aliphatic group optionally interrupted with one or more oxygen atoms, Q is $CF_3$ or F, R is an aliphatic or aromatic hydrocarbon group, G represents a carboxylic or sulphonic acid or salt thereof, t is 0 or 1 and n is 1, 2 or 3. Generally, the fluorinated surfactant of formula (I) will be a low molecular weight compound, for example a compound having a molecular weight for the anion part of the compound of not more than 1000 g/mol, typically not more than 600 g/mol and in particular embodiments, the anion of the fluorinated surfactant may have a molecular weight of not more than 500 g/mol.

Particularly preferred fluorinated surfactants according to formula (I) are those that when administered to rats show a recovery of at least 45%, for example at least 50% of the administered amount after 96 hours via renal elimination and that have a renal elimination half-life of not more than 35 hours, for example of not more than 30 hours in rats as tested according to the method set forth in the examples. Generally, fluorinated surfactants in which each of the fluorinated aliphatic moieties in the compound have not more than 3 carbon atoms fulfill the aforementioned conditions of renal recovery and half-life. Thus, preferred compounds are those in which the terminating fluorinated alkyl group of the compound has not more than 3 carbon atoms.

It has been found that these surfactants can be easily and conveniently be prepared in a cost effective way and generally can be used to fulfill one or more of the desires discussed above. In particular, the fluorinated surfactants of formula (I) have been found to be suitable in the aqueous emulsion polymerization of monomers, in particular fluorinated monomers. In addition to their use in aqueous emulsion polymerization, the fluorinated surfactants may be useful in other applications where surfactants are used, such as for example in coating compositions or in stabilizing dispersions including for example fluoropolymer dispersions.

In a further aspect, the present invention provides an intermediate product suitable for use in the synthesis of a fluorinated surfactant according to above formula (I), the intermediate product corresponding to the general formula:

$$[R_f-(O)_t-CQH-CF_2-O]_n-R-Z \quad (II)$$

wherein $R_f$ represents a partially or fully fluorinated aliphatic group optionally interrupted with one or more oxygen atoms, Q is F or $CF_3$, R is an aliphatic or aromatic hydrocarbon group, Z represents a carboxylic acid ester, carboxylamide, sulphonamide, or sulphonic acid ester, t is 0 or 1 and n is 1, 2 or 3.

According to another aspect of the invention, there is provided a method for making the above intermediate product of formula (II), the method comprising reacting, generally in the presence of a base, (a) a fluorinated olefin of the general formula:

$$R_f-(O)_t-CF=CF_2$$

wherein $R_f$ and t are as defined above;
with (b) an organic compound of the formula:

$$(HO)_n-R-Z$$

wherein n is 1, 2 or 3, Z and R are as defined above.

In one aspect of the present invention, the intermediate product of formula (II) is used to make a fluorinated surfactant of formula (I) by hydrolyzing the intermediate product to its corresponding acid or salt.

In an alternative embodiment, the fluorinated surfactant of formula (I) may be prepared by a method comprising reacting, generally in the presence of a base, (a) a fluorinated olefin of the general formula:

$$R_f-(O)_t-CF=CF_2$$

wherein $R_f$ and t are as defined above;
with (b) an organic compound of the formula:

$$(HO)_n-R-G$$

wherein n is 1, 2 or 3, G and R are as defined above.

Still further, in a particular aspect, the invention provides a method for making a fluoropolymer comprising an aqueous emulsion polymerization of one or more fluorinated monomers wherein said aqueous emulsion polymerization is carried out in the presence of one or more fluorinated surfactants according to formula (I) above.

In yet a further aspect, the present invention provides an aqueous composition comprising one or more fluorinated surfactants according to formula (I) above.

In a still further aspect, the present invention provides a method of applying the above defined aqueous composition to a substrate. Suitable substrates include for example metal substrates, glass, plastic or fabrics.

DETAILED DESCRIPTION

Fluorinated surfactants according to formula (I) may be used in a variety of applications where a surfactant is needed or desired. The fluorinated surfactants according to formula (I) have been found to be suitable for use in an aqueous emulsion polymerization of fluorinated and/or non-fluorinated monomers. In particular, the fluorinated surfactants can be used in the aqueous emulsion polymerization of fluorinated monomers, e.g. fluorinated olefins, to make fluoropolymers that have a partially or fully fluorinated backbone.

The $R_f$ group in formula (I) above represents a partially or fully fluorinated linear or branched aliphatic group that may be interrupted with one or more oxygen atoms. In a particular embodiment, the $R_f$ group will have from 1 to 50 carbon atoms, for example between 3 and 30 carbon atoms. Generally, a fully fluorinated $R_f$ group will be preferred when the surfactant is to be used in the aqueous emulsion polymerization of fluorinated monomers to make fluoropolymers with a partially or fully fluorinated backbone. Thus, for the aqueous emulsion polymerization, surfactants according to formula (I) are preferred in which $R_f$ is a linear or branched perfluorinated aliphatic group optionally interrupted with one or more oxygen atoms. For environmental reasons, it will generally be preferred that a perfluorinated aliphatic $R_f$ group does not contain alkyl and/or alkylene fragments of more than 6 carbon atoms, typically not more than 4 carbon atoms.

In a particular embodiment, the $R_f$ is selected from the group consisting of linear or branched perfluorinated aliphatic groups of 1 to 4, 5 or 6 carbon atoms, perfluorinated groups of the formula $R_f^1-[OR_f^2]_p-[OR_f^3]_q-$ wherein $R_f^1$ is a linear or branched perfluorinated aliphatic group of 1 to 4, 5 or 6 carbon atoms, $R_f^2$ and $R_f^3$ each independently represents linear or branched a perfluorinated alkylene of 1, 2, 3 or 4 carbon atoms and p and q each independently represent a value of 0 to 4 and wherein the sum of p and q is at least 1 and perfluorinated groups of the formula $R_f^4-[OR_f^5]_k-[OR_f^6]_m-O-CF_2-$ wherein $R_f^4$ is a linear or branched perfluorinated aliphatic group of 1 to 4, 5 or 6 carbon atoms, $R_f^5$ and $R_f^6$ each independently represents a linear or branched perfluorinated alkylene of 1, 2, 3 or 4 carbon atoms and k and m each independently represent a value of 0 to 4.

The group R in formula (I) of the fluorinated surfactant includes linear, branched or cyclic aliphatic and aromatic groups. Examples of aliphatic groups include alkylene groups of 1 to 4 carbon atoms such as for example methylene. Examples of aromatic groups include phenyl groups including phenyl groups that may have one or more substituents such as halogens and alkyl groups. Depending on the valence of R, the fluorinated surfactant may contain 1, 2 or 3 $R_f$ groups as indicated by the index n in formula (I).

The group G in formula (I) represents a carboxylic acid or a sulphonic acid group or a salt of any such acids. Suitable salts include ammonium salts including $NH_4^+$ salts as well as organic ammonium salts; metal salts including alkali metal salts such as sodium, lithium and potassium salts and earth alkali metal salts such as calcium and magnesium salts.

In a particular embodiment, the fluorinated surfactant according to formula (I) corresponds to the formula:

$$R_f-(O)_t-CQH-CF_2-O-CH_2-G \quad (III)$$

wherein $R_f$, Q, t and G have the same meaning as defined above. In a particular embodiment, the fluorinated surfactant is one according to formula (III) wherein Q is F.

In a further embodiment, the fluorinated surfactant according to formula (I) corresponds to the formula:

$$[R_f-(O)_t-CQH-CF_2-O]_n-Ph-G \quad (IV)$$

wherein $R_f$, Q, t, n and G have the same meaning as defined above and wherein Ph represents a benzene ring. In this particular embodiment, n is generally 1 and the substituents G and fluorinated ether fragment of the molecule may be positioned ortho, meta or para relative to each other. Also in a typical embodiment of formula (IV), the group Q is F.

In a particular embodiment, the fluorinated surfactant is a fluorinated surfactant according to formula (I), (III) or (IV) with t being 1 and wherein $R_f$ is selected from the group consisting of linear or branched perfluorinated aliphatic groups of 1 to 4, 5 or 6 carbon atoms and perfluorinated groups of the formula $R_f^1-[OR_f^2]_p-[OR_f^3]_q-$ wherein $R_f^1$ is a linear or branched perfluorinated aliphatic group of 1 to 4, 5 or 6 carbon atoms, $R_f^2$ and $R_f^3$ each independently represents a linear or branched perfluorinated alkylene of 1, 2, 3 or 4 carbon atoms and p and q each independently represent a value of 0 to 4 and wherein the sum of p and q is at least 1.

In a particular embodiment, the fluorinated surfactant is a fluorinated surfactant according to formula (I), (III) or (IV) with t being 0 and wherein $R_f$ is selected from the group consisting of linear or branched perfluorinated aliphatic groups of 1 to 4, 5 or 6 carbon atoms and perfluorinated groups of the formula $R_f^4-[OR_f^5]_k-[OR_f^6]_m-O-CF_2-$ wherein $R_f^4$ is a perfluorinated aliphatic group of 1 to linear or branched carbon atoms, $R_f^5$ and $R_f^6$ each independently represents a linear or branched perfluorinated alkylene of 1, 2, 3 or 4 carbon atoms and k and m each independently represent a value of 0 to 4.

Specific examples of fluorinated surfactants according to formula (I) include:

$C_3F_7-O-CHF-CF_2-OC_6H_4COO^-Li^+$
$C_3F_7-O-CF_2-CF_2-O-CHF-CF_2-OC_6H_4COO^-Na^+$
$C_3F_7-O-CF_2-CF_2-CF_2-O-CHF-CF_2-OC_6H_4COOH$
$C_3F_7-O-CF_2-CHF-CF_2-OC_6H_4COO^-NH_4^+$
$C_3F_7-CF_2-CHF-CF_2-OC_6H_4COO^-NH_4^+$
$C_3F_7-O-CHF-CF_2-OCH_2COO^-Li^+$
$C_3F_7-O-CF_2-CF_2-O-CHF-CF_2-OCH_2COO^-Na^+$
$C_3F_7-O-CF_2-CF_2-CF_2-O-CHF-CF_2-OCH_2COOH$
$C_3F_7-O-CF_2-CHF-CF_2-OCH_2COO^-NH_4^+$
$C_3F_7-CF_2-CHF-CF_2-OCH_2COO^-NH_4^+$
$C_3F_7-O-CHF-CF_2-OC_6H_4SO_3H$
$CF_3-CH(CF_3)-CF_2-O-CH_2-COOH$
$C_3F_7-O-C(CF_3)F-CF_2-O-CFH-CF_2-O-CH_2-COOH$
$CF_3-CFH-CF_2-O-C_6H_4-COOH$

The fluorinated surfactants can be readily prepared by hydrolyzing the intermediate compound of formula (II) above. In formula (II) above, Z represents a carboxylic or sulphonic acid ester or a carboxylamide or sulphonamide. Typically a carboxylic acid ester or sulphonic acid ester is used. In one embodiment, the ester can be an aliphatic ester, e.g. an alkyl ester in which the number of carbon atoms in the alkyl group are from 1 to 4. Alternatively, the ester can also be an aromatic ester such as for example a phenyl or benzyl ester. Hydrolysis of the intermediate compound may be carried out under acidic or basic conditions and is generally carried out in an alcoholic acidic or basic solution of the intermediate compound. Alternatively the intermediate compound may be hydrolysed in an acidic or basic solution of other water miscible organic solvents such as ketones, ethers etc. Typically, a basic alcoholic solution is used such as for example a methanol or ethanol solution containing an alkali metal hydroxide as the base. Typically the hydrolysis is carried out at room temperature but it is also possible to use elevated temperatures of for example up to the boiling point of the solution.

The intermediate compound according to formula (II) can be prepared by reacting a fluorinated olefin of the general formula:

$$R_f-(O)_t-CF=CF_2 \quad (V)$$

wherein $R_f$ and t are as defined above, with an organic compound of the formula:

$$(HO)_n-R-Z \quad (VI)$$

wherein n is 1, 2 or 3, Z and R are as defined above. Compounds according to formula (V) are well known in the art and include fluorinated olefins such as perfluorinated alkyl vinyl compounds, vinyl ethers in particular perfluorovinyl ethers and allyl ethers, in particular perfluorinated allyl ethers. Compounds according to formula (VI) are also well known in the art and/or are commercially available. The reaction of compound (V) with compound (VI) is typically carried out in the presence of a base although it is also possible to carry out the reaction under acidic or neutral conditions. Suitable bases include carbonates such as potassium carbonate, sodium carbonate and lithium carbonate, hydroxides, alkoholates etc. The amount of base used may vary widely. For example a catalytic amount may be used. Generally the amount of base used will be about at least 1 or 2% by weight based on the amount of reactant of formula (VI). In a particular embodiment, the amount of base can be up to 2 times the molar amount of the reactant of formula (VI). The reaction is typically carried out in an aprotic solvent such as for example, tetrahydrofuran, acetonitrile, glyme, diglyme etc. Further suitable aprotic solvents are disclosed in DE 3828063. The reaction is typically carried out at a temperature between 0 and 200° C., for example between 10 and 150° C. The reaction is generally carried out at an ambient pressure (1 bar) or up to 20 bar. Following the reaction, the resulting compound may be isolated and purified by distillation.

Alternatively, the fluorinated surfactant may be prepared by reacting the fluorinated olefin of formula (V) above with a hydroxy substituted carboxylic or sulphonic acid or salt thereof. Thus, in accordance with this embodiment the fluorinated olefin of formula (V) is reacted with a compound of the formula:

$$(HO)_n-R-G \quad (VII)$$

wherein n is 1, 2 or 3, G and R are as defined above. The reaction of a fluorinated olefin of formula (V) with a hydroxy compound or formula (VII) can be carried out under the same conditions described above for the reaction with compounds of formula (VI).

In a particular preferred embodiment, one or more fluorinated surfactants of formula (I) are used in the aqueous emulsion polymerization of one or more fluorinated monomers, in particular gaseous fluorinated monomers. By gaseous fluorinated monomers is meant monomers that are present as a gas under the polymerization conditions. In a particular embodiment, the polymerization of the fluorinated monomers is started in the presence of the fluorinated surfactant according to formula (I), i.e. the polymerization is initiated in the presence of the fluorinated surfactant. The amount of fluorinated surfactant used may vary depending on desired properties such as amount of solids, particle size etc. Generally the amount of fluorinated surfactant will be between 0.001% by weight based on the weight of water in the polymerization and 5% by weight, for example between 0.005% by weight and 2% by weight. A practical range is between 0.005% by weight and 1% by weight. While the polymerization is generally initiated in the presence of fluorinated surfactant, it is not excluded to add further fluorinated surfactant during the polymerization although such will generally not be necessary. Nevertheless, it may be desirable to add certain monomer to the polymerization in the form of an aqueous emulsion. For example, fluorinated monomers and in particular perfluorinated co-monomers that are liquid under the polymerization conditions may be advantageously added in the form of an aqueous emulsion. Such emulsion of such co-monomers is preferably prepared using the fluorinated surfactant according to formula (I) as an emulsifier.

In accordance with a particular embodiment of the present invention, a mixture of fluorinated surfactants according to formula (I) is used. In a still further embodiment the fluorinated surfactant according to formula (I) or mixture thereof may be used in combination with one or more further fluorinated surfactants that do not correspond to formula (I). In a particular embodiment, such further fluorinated surfactants include perfluoroalkanoic acids, in particular those that have not more than 6 carbon atoms or not more than 4 carbon atoms. In a further embodiment, such further fluorinated surfactants include perfluorinated ethers and perfluorinated polyethers. Suitable perfluorinated polyethers include those according to the following formulas (VIII) or (IX):

$$CF_3—(OCF_2)_m—O—CF_2—X \qquad (VIII)$$

wherein m has a value of 1 to 6 and X represents a carboxylic acid group or salt thereof;

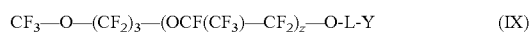

$$CF_3—O—(CF_2)_3—(OCF(CF_3)—CF_2)_z—O-L-Y \qquad (IX)$$

wherein z has a value of 0, 1, 2 or 3, L represents a divalent linking group selected from —CF(CF$_3$)—, —CF$_2$— and —CF$_2$CF$_2$— and Y represents a carboxylic acid group or salt thereof. Examples of carboxylic acid salts include sodium, potassium and ammonium (NH$_4$) salts. Still further polyethers include those disclosed in U.S. Pat. No. 3,271,341; U.S. Publication No. 2005/0090613, U.S. Pat. No. 4,864,006; U.S. Pat. No. 4,789,717 and EP 625526. Examples of perfluorinated ether surfactants that can be used include those according to the following general formula:

$$R^7_f—O—CF_2CF_2—X \qquad (X)$$

wherein $R^7_f$ represents a linear or branched perfluoroalkyl group having 1, 2, 3 or 4 carbon atoms and X represents a carboxylic acid group or salt thereof. Examples of carboxylic acid salts include sodium, potassium and ammonium (NH$_4$) salts.

When the fluorinated surfactant(s) according to formula (I) are used in admixture with one or more further fluorinated surfactants, the fluorinated surfactant(s) of formula (I) may be present in a weight ratio of for example 1:10 to 100:1. Generally, when such a mixture is used it will be preferred that the fluorinated surfactant(s) according to formula (I) represents at least 20%, for example at least 30% or at least 51% by weight of the total amount of fluorinated surfactant used.

The aqueous emulsion polymerization may be carried out at temperatures between 10 to 15° C., preferably 20° C. to 110° C. and the pressure is typically between 2 and 30 bar, in particular 5 to 20 bar. The reaction temperature may be varied during the polymerization to influence the molecular weight distribution, i.e., to obtain a broad molecular weight distribution or to obtain a bimodal or multimodal molecular weight distribution. The pH of the polymerization medium may vary widely and is generally in the range of 2 to 11. Considering the pKa of the acid group of the fluorinated surfactant of formula (I), a pH of at least 5 will generally be preferred, in particular of the fluorinated surfactant of formula (I) is used without the use of other fluorinated surfactants. Accordingly, a typical pH range may be from 5 to 10 or from 6 to 10.

The aqueous emulsion polymerization is typically initiated by an initiator including any of the initiators known for initiating a free radical polymerization of fluorinated monomers. Suitable initiators include peroxides and azo compounds and redox based initiators. Specific examples of peroxide initiators include, hydrogen peroxide, sodium or barium peroxide, diacylperoxides such as diacetylperoxide, disuccinyl peroxide, dipropionylperoxide, dibutyrylperoxide, dibenzoylperoxide, benzoylacetylperoxide, diglutaric acid peroxide and dilaurylperoxide, and further per-acids and salts thereof such as e.g. ammonium, sodium or potassium salts. Examples of per-acids include peracetic acid. Esters of the peracid can be used as well and examples thereof include tert.-butylperoxyacetate and tert.-butylperoxypivalate. Examples of inorganic include for example ammonium-alkali- or earth alkali salts of persulfates, permanganic or manganic acid or manganic acids. A persulfate initiator, e.g. ammonium persulfate (APS), can be used on its own or may be used in combination with a reducing agent. Suitable reducing agents include bisulfites such as for example ammonium bisulfite or sodium metabisulfite, thiosulfates such as for example ammonium, potassium or sodium thiosulfate, hydrazines, azodicarboxylates and azodicarboxyldiamide (ADA). Further reducing agents that may be used include sodium formaldehyde sulfoxylate (Rongalit®) or fluoroalkyl sulfinates as disclosed in U.S. Pat. No. 5,285,002. The reducing agent typically reduces the half-life time of the persulfate initiator. Additionally, a metal salt catalyst such as for example copper, iron or silver salts may be added. The amount of initiator may be between 0.01% by weight (based on the fluoropolymer solids to be produced) and 1% by weight. In one embodiment, the amount of initiator is between 0.05 and 0.5% by weight. In another embodiment, the amount may be between 0.05 and 0.3% by weight.

The aqueous emulsion polymerization system may further comprise other materials, such as buffers and, if desired, complex-formers or chain-transfer agents. Examples of chain transfer agents that can be used include esters such diethylmalonate, ethers such as dimethyl ether, methyl t-butyl ether, alkanes having 1 to 5 carbon atoms such as ethane, propane and n-pentane, halogenated hydrocarbons such as CCl$_4$, CHCl$_3$ and CH$_2$Cl$_2$ and hydrofluorocarbon compounds such as CH$_2$F—CF$_3$ (R134a).

Examples of fluorinated monomers that may be polymerized using the fluorinated surfactant according to formula (I) as an emulsifier include partially or fully fluorinated gaseous monomers including fluorinated olefins such as tetrafluoroethylene (TFE), chlorotrifluoroethylene (CTFE), hexafluoropropylene (HFP), vinyl fluoride (VF), vinylidene fluoride (VDF), partially or fully fluorinated allyl ethers and partially or fully fluorinated vinyl ethers. The polymerization may further involve non-fluorinated monomers such as ethylene and propylene.

Further examples of fluorinated monomers that may be used in the aqueous emulsion polymerization according to the invention include those corresponding to the formula:

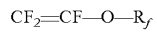

$$CF_2=CF—O—R_f$$

wherein $R_f$ represents a perfluorinated aliphatic group that may contain one or more oxygen atoms. Preferably, the perfluorovinyl ethers correspond to the general formula:

$CF_2=CFO(R_fO)_n(R'_fO)_mR''_f$ wherein $R_f$ and $R'_f$ are different linear or branched perfluoroalkylene groups of 2-6 carbon atoms, m and n are independently 0-10, and $R''_f$ is a perfluoroalkyl group of 1-6 carbon atoms. Examples of perfluorovinyl ethers according to the above formulas include perfluoro-2-propoxypropylvinyl ether (PPVE-2), perfluoro-3-methoxy-n-propylvinyl ether, perfluoro-2-methoxy-ethylvinyl ether, perfluoromethylvinyl ether (PMVE), perfluoro-n-propylvinyl ether (PPVE-1) and $CF_3$—$(CF_2)_2$—$O$—$CF(CF_3)$—$CF_2$—$O$—$CF(CF_3)$—$CF_2$—$O$—$CF=CF_2$.

Still further, the polymerization may involve comonomers that have a functional group such as for example a group capable of participating in a peroxide cure reaction. Such functional groups include halogens such as Br or I as well as nitrile groups. Specific examples of such comonomers that may be listed here include (a) bromo- or iodo-(per)fluoroalkyl-(per)fluorovinylethers having the formula:

$Z$-$R_f$—$O$—$CX=CX_2$ wherein each X may be the same or different and represents H or F, Z is Br or I, $R_f$ is a (per)fluoroalkylene $C_1$-$C_{12}$, optionally containing chlorine and/or ether oxygen atoms; for example: $BrCF_2$—$O$—$CF=CF_2$, $BrCF_2CF_2$—$O$—$CF=CF_2$, $BrCF_2CF_2CF_2$—$O$—$CF=CF_2$, $CF_3CFBrCF_2$—$O$—$CF=CF_2$, and the like; and (b) bromo- or iodo containing fluoroolefins such as those having the formula:

$Z'$-$(R_f')_r$—$CX=CX_2$, wherein each X independently represents H or F, Z' is Br or I, $R_f'$ is a perfluoroalkylene $C_1$-$C_{12}$, optionally containing chlorine atoms and r is 0 or 1; for instance: bromotrifluoroethylene, 4-bromo-perfluorobutene-1, and the like; or bromofluoroolefins such as 1-bromo-2,2-difluoroethylene and 4-bromo-3,3,4,4-tetrafluorobutene-1.

Examples of nitrile containing monomers that may be used include those that correspond to one of the following formulas:

$CF_2=CF$—$CF_2$—$O$—$R_f$—$CN$ $CF_2=CFO(CF_2)_LCN$ $CF_2=CFO[CF_2CF(CF_3)O]_g(CF_2)_vOCF(CF_3)CN$ $CF_2=CF[OCF_2CF(CF_3)]_kO(CF_2)_uCN$ wherein L represents an integer of 2 to 12; g represents an integer of 0 to 4; k represents 1 or 2; v represents an integer of 0 to 6; u represents an integer of 1 to 6, $R_f$ is a perfluoroalkylene or a bivalent perfluoroether group. Specific examples of nitrile containing liquid fluorinated monomers include perfluoro(8-cyano-5-methyl-3,6-dioxa-1-octene), $CF_2=CFO(CF_2)_5CN$, and $CF_2=CFO(CF_2)_3OCF(CF_3)CN$.

The aqueous emulsion polymerization may be used to produce a variety of fluoropolymers including perfluoropolymers, which have a fully fluorinated backbone, as well as partially fluorinated fluoropolymers. Also the aqueous emulsion polymerization may result in melt-processible fluoropolymers as well as those that are not melt-processible such as for example polytetrafluoroethylene and so-called modified polytetrafluoroethylene. The polymerization process can further yield fluoropolymers that can be cured to make fluoroelastomers as well as fluorothermoplasts. Fluorothermoplasts are generally fluoropolymers that have a distinct and well noticeable melting point, typically in the range of 60 to 320° C. or between 100 and 320° C. They thus have a substantial crystalline phase. Fluoropolymers that are used for making fluoroelastomers typically are amorphous and/or have a neglectable amount of crystallinity such that no or hardly any melting point is discernable for these fluoropolymers.

The aqueous emulsion polymerization results in a dispersion of the fluoropolymer in water. Generally the amount of solids of the fluoropolymer in the dispersion directly resulting from the polymerization will vary between 3% by weight and about 40% by weight depending on the polymerization conditions. A typical range is between 5 and 30% by weight, for example between 10 and 25% by weight. The particle size (volume average diameter) of the fluoropolymer is typically between 40 nm and 400 nm with a typical particle size being between 60 nm and about 350 nm. The total amount of fluorinated surfactant according to formula (I) in the resulting dispersion is typically between 0.001 and 5% by weight based on the amount of fluoropolymer solids in the dispersion. A typical amount may be from 0.01 to 2% by weight or from 0.02 to 1% by weight.

The fluoropolymer may be isolated from the dispersion by coagulation if a polymer in solid form is desired. Also, depending on the requirements of the application in which the fluoropolymer is to be used, the fluoropolymer may be post-fluorinated so as to convert any thermally unstable end groups into stable $CF_3$ end groups. The fluoropolymer may be post-fluorinated as described in for example EP 222945. Generally, the fluoropolymer will be post fluorinated such that the amount of end groups in the fluoropolymer other than $CF_3$ is less than 80 per million carbon atoms.

For coating applications, an aqueous dispersion of the fluoropolymer is desired and hence the fluoropolymer will not need to be separated or coagulated from the dispersion. To obtain a fluoropolymer dispersion suitable for use in coating applications such as for example in the impregnation of fabrics or in the coating of metal substrates to make for example cookware, it will generally be desired to add further stabilizing surfactants and/or to further increase the fluoropolymer solids. For example, anionic and/or non-ionic stabilizing surfactants may be added to the fluoropolymer dispersion. These stabilizing are typically non-fluorinated. Typically these will be added thereto in an amount of 1 to 12% by weight based on fluoropolymer solids. Examples of non-ionic surfactants that may be added include $$R^1\text{—}O\text{—}[CH_2CH_2O]_n\text{—}[R^2O]_m\text{—}R^3 \quad (XI)$$

wherein $R^1$ represents an aromatic or linear or branched aliphatic hydrocarbon group having at least 8 carbon atoms, $R^2$ represents an alkylene having 3 carbon atoms, $R^3$ represents hydrogen or a $C_1$-$C_3$ alkyl group, n has a value of 0 to 40, m has a value of 0 to 40 and the sum of n+m being at least 2. It will be understood that in the above formula (XI), the units indexed by n and m may appear as blocks or they may be present in an alternating or random configuration. Examples of non-ionic surfactants according to formula (XI) above include alkylphenol oxy ethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which $R^1$ in the above formula (XI) represents an alkyl group of 4 to 20 carbon atoms, m is 0 and $R^3$ is hydrogen. An example thereof includes isotridecanol ethoxylated with about 8 ethoxy groups and which is commercially available as GENAPOL®080 from Clariant GmbH. Non-ionic surfactants according to formula (XI) in which the hydrophilic part comprises a block-copolymer of ethoxy groups and propoxy groups may be used as well. Such non-ionic surfactants are commercially available from Clariant GmbH under the trade designation GENAPOL® PF 40 and GENAPOL® PF 80.

The amount of fluoropolymer solids in the dispersion may be upconcentrated as needed or desired to an amount between 30 and 70% by weight. Any of the known upconcentration techniques may be used including ultrafiltration and thermal upconcentration.

The invention is further illustrated with reference to the following examples without the intention to limit the invention thereto.

EXAMPLES

Test Methods

Determination of Solid Content
Determination of solid content was carried out subjecting the sample to a temperature up to 250° C. for 30 min.

Determination of Particle Size
Particle size was measured via inelastic light scattering using the Malvern 1000 HAS Zetasizer. The reported particle size is the volume average diameter.

Determination of Melt Flow Index (MFI)
The melt flow index (MFI) was measured according to DIN 53735, ISO 12086 or ASTM D-1238 at a support weight of 5.0 kg. Unless otherwise noted, a temperature of 265° C. was applied. The MFIs cited here were obtained with a standardized extrusion die of 2.1 mm diameter and a length of 8.0 mm.

Example 1

Synthesis of $C_3F_7$—O—$C_2HF_3$—$OC_6H_4COO^-Li^+$ 105 g Perfluoropropyl vinylether (PPVE-1) was added dropwise to a mixture of 1400 ml Acetonitrile, 106 g 4-Hydroxy benzoic methylester and 97 g $K_2CO_3$; the temperature was maintained between 25-30° C. After the complete addition of PPVE-1, the reaction mixture was agitated for another 1 hour. After striping the solvent, the methylester $C_3F_7$—O—$C_2HF_3$—O—$C_6H_4$—$COOCH_3$ (1) was distilled under reduced pressure (3 mbar, bp. 97-102° C.); yield 64% (1).

A 10 wt % methanol solution of (1) was agitated with an aqu. 5% LiOH-solution to convert (1) into the Li+ salt. Methanol/water was removed by distillation, until a 30% solution of the Li-salt of (1) was achieved; the methanol content of the Li-salt solution was below 100 ppm prior use for polymerizations.

Example 2

Synthesis of $C_3F_7$—O—$C_2HF_3$—O—$CH_2$—$COO^-NH_4$

A mixture of 320 ml Tetrahydrofurane, 40 g Hydroxy acetic methylester and 118 g PPVE-1 is cooled to 0° C., 27 g KOH-powder are added in small portions—during the addition of KOH, the reaction mixture heats up to 60° C. After the addition of KOH, the whole reaction mixture is agitated for 6 h at 25° C. The precipitated salt is separated by filtration, dissolved in 300 ml water and then treated with 57 g $H_2SO_4$ (conc). The resulting mixture separates in two layers; the lower phase is $C_3F_7$—O—$C_2HF_3$—O—$CH_2$—COOH (2), 86 g (56%).

The distilled acid (2) (bp. 125° C., 20 mbar) is neutralized with 25% aqueous ammonia solution to provide a 30% solution of (2) in water.

Comparative Example 1

Polymerization of THV with APFO 28 l deionized water containing 2 g ammonium perfluorooctanoic acid (APFO) were fed in a 50 l polymerization vessel together with 100 g NaOH and 0.1 mg CuSO4. Air was removed by alternating evacuation and pressurizing with nitrogen up to 4 bar. Then the vessel was pressurized with 6.4 bar HFP, 5.2 bar VDF, 3.7 bar TFE and 0.1 bar ethane. The temperature in the vessel is adjusted to 70° C. Polymerization was initiated by pumping in the vessel an aqueous solution containing 36 g ammonium persulfate (APS) dissolved in 100 ml deionized water and a solution of 6 g $Na_2S_2O_5$ in 50 ml deionized water. The speed of agitation was 240 rpm. Polymerization temperature and pressure were kept constant by feeding TFE, HFP and VDF in a constant ratio of 1:0.455: 0.855. When 3.5 kg TFE were consumed, polymerization was stopped by closing the monomer-feeding and lowering the speed of agitation. The vessel was vented and the resulting dispersion discharged. The thus obtained dispersion had a solid content of 23% and particle size of about 271 nm.

Example 3

Polymerization of THV with Emulsifier from Example 1

28 l deionized water containing 2 g of emulsifier of Example 1 were fed in a 50 l polymerization vessel together with 100 g NaOH and 0.1 mg CuSO4. Air was removed by alternating evacuation and pressurizing with nitrogen up to 4 bar. Then the vessel was pressurized with 6.4 bar HFP, 5.2 bar VDF, 3.7 bar TFE and 0.1 bar ethane. The temperature in the vessel is adjusted to 70° C. Polymerization was initiated by pumping in the vessel an aqueous solution containing 36 g APS dissolved in 100 ml deionized water and a solution of 6 g $Na_2S_2O_5$ in 50 ml deionized water. The speed of agitation was 240 rpm. Polymerization temperature and pressure were kept constant by feeding TFE, HFP and VDF in a constant ratio of 1:0.455:0.855. When 3.5 kg TFE were consumed, polymerization was stopped by closing the monomer-feeding and lowering the speed of agitation. The vessel was vented and the resulting dispersion discharged. The thus obtained dispersion had a solid content of 22% and particle size of about 226 nm. The MFI(265° C./5 kg) was 0.04.

Example 4

Polymerization of THV with Emulsifier from Example 2

28 l deionized water containing 2 g of the emulsifier from Example 2 were fed in a 50 l polymerization vessel together with 100 g NaOH and 0.1 mg CuSO4. Air was removed by alternating evacuation and pressurizing with nitrogen up to 4 bar. Then the vessel was pressurized with 6.4 bar HFP, 5.2 bar VDF, 3.7 bar TFE and 0.1 bar ethane. The temperature in the vessel was adjusted to 70° C. Polymerization was initiated by pumping in the vessel an aqueous solution containing 36 g APS dissolved in 100 ml deionized water and a solution of 6 g $Na_2S_2O_5$ in 50 ml deionized water. The speed of agitation was 240 rpm. Polymerization temperature and pressure were kept constant by feeding TFE, HFP and VDF in a constant ratio of 1:0.455:0.855. When 3.5 kg TFE are consumed, polymerization was stopped by closing the monomer-feeding and lowering the speed of agitation. The vessel was vented and the resulting dispersion discharged. The thus obtained dispersion had a solid content of 22% and particle size of about 248 nm. The MFI(265° C./5 kg) was 0.1.

Determination of Bio-Accumulation

The emulsifier from Example 2 was evaluated for urinary clearance using a pharmacokinetic study in rats. The goal was to measure the total amount of parent compound eliminated via urinary output and estimate the rate of elimination. The study was approved by the IACUC (Institutional Animal Care and Use Committees) and was performed in 3M Company's AAALAC (Association for Assessment and Accreditation of Laboratory Animal Care)—accredited facility.

The study utilized male Sprague Dawley rats, 6 to 8 weeks of age, and approximately 200 to 250 g body weight at study onset. The test compounds of table 2 were administered at a dose of 73 micro Moles per kg body weight in rats (N=3 animals per tested compound). All test compounds were prepared in sterile deionized water and given to rats via oral gavage. After test compounds administration, the rats were housed individually in metabolism cages for urine collection: 0 to 6 hours, 6 to 24 hours, 24 to 48 hours and 72 to 96 hours. Animals were observed throughout the study for clinical signs of toxicity. Gross necropsy was performed at the termination of each study (96 hours post-dose) with sera and liver samples being retained from each animal.

The concentration of the parent compound or metabolites thereof were quantitatively measured via fluorine NMR on each urine sample for each animal at each time point based on internally added standards.

The bioaccumulation data obtained in accordance with the above test are reported in table 2 below.

TABLE 2

| | T ½ (h) | % Recovery (96 h) | Compound-related Effects |
|---|---|---|---|
| APFO | ~550 | 6 | Hepatomegaly |
| Example 2 | 13* | 65* | — |

* No parent compound observed in the urine. T ½ and % recovery are based on elimination of the major metabolite—$C_3F_7$—O—CHFCOO⁻. $T_{1/2}$ is the renal half-life and is the time required for the amount of a particular substance in a biological system to be reduced to one half of its value by biological processes when the rate of removal is approximately exponential. In these examples the value of $T_{1/2}$ is calculated by exponential least squares curve fitting ($y=Ae^{Bx}$ and $T_{1/2}=0.693/B$) where y represents the concentration of analyte in urine and x represents time in hours.

The invention claimed is:

1. Aqueous composition comprising one or more fluorinated surfactants having the general formula:

$$[R_f—(O)_t—CQH—CF_2—O]_n—R—G \quad (I)$$

wherein $R_f$ represents a partially or fully fluorinated aliphatic group optionally interrupted with one or more oxygen atoms, Q represents F or $CF_3$, R is an aliphatic or aromatic hydrocarbon group, G represents a carboxylic or sulphonic acid or salt thereof, t is 0 or 1 and n is 1, 2 or 3.

2. Aqueous composition according to claim 1 wherein $R_f$ represents a perfluorinated aliphatic group that is optionally interrupted with one or more oxygen atoms.

3. Aqueous composition according to claim 1 wherein the fluorinated surfactant corresponds to the following general formula:

$$R_f—(O)_t—CQH—CF_2—O—CH_2—G \quad (III)$$

wherein $R_f$, Q, G and t are as defined in claim 1.

4. Aqueous composition according to claim 1 wherein the fluorinated surfactant corresponds to the following general formula:

$$[R_f—(O)_t—CQH—CF_2—O]_n—Ph—G \quad (IV)$$

wherein $R_f$, Q, G, t and n are as defined in claim 1 and wherein Ph represents a benzene ring.

5. Aqueous composition according to claim 1 wherein t is 1 and wherein $R_f$ is selected from the group consisting of linear or branched perfluorinated aliphatic groups of 1 to 6 carbon atoms and perfluorinated groups of the formula:

$$R_f^1—[OR_f^2]_p—[OR_f^3]_q—$$

wherein $R_f^1$ is a linear or branched perfluorinated aliphatic group of 1 to 6 carbon atoms, $R_f^2$ and $R_f^3$ each independently represents a linear or branched perfluorinated alkylene of 1, 2, 3 or 4 carbon atoms and p and q each independently represent a value of 0 to 4 and wherein the sum of p and q is at least 1.

6. Aqueous composition according to claim 1 wherein t is 0 and wherein $R_f$ is selected from the group consisting of linear or branched perfluorinated aliphatic groups of 1 to 6 carbon atoms and perfluorinated groups of the formula:

$$R_f^4—[OR_f^5]_k—[OR_f^6]_m—O—CF_2—$$

wherein $R_f^4$ is a linear or branched perfluorinated aliphatic group of 1 to 6 carbon atoms, $R_f^5$ and $R_f^6$ each independently represents a linear or branched perfluorinated alkylene of 1, 2, 3 or 4 carbon atoms and k and m each independently represent a value of 0 to 4.

7. Method for making a fluoropolymer comprising an aqueous emulsion polymerization of one or more fluorinated monomers wherein said aqueous emulsion polymerization is carried out using the aqueous composition as defined in claim 1.

8. Method according to claim 7 wherein the amount of said one or more fluorinated surfactants is between 0.001 and 5% by weight based on the amount of water in the aqueous phase of the aqueous emulsion polymerization.

9. Method according to claim 7 wherein said aqueous emulsion polymerization further comprises one or more fluorinated surfactants other than said fluorinated surfactants having the general formula:

$$[R_f—(O)_t—CQH—CF_2—O]_n—R—G \quad (I)$$

wherein $R_f$ represents a partially or fully fluorinated aliphatic group optionally interrupted with one or more oxygen atoms, Q represents F or $CF_3$, R is an aliphatic or aromatic hydrocarbon group, G represents a carboxylic or sulphonic acid or salt thereof, t is 0 or 1 and n is 1, 2 or 3.

10. Method according to claim 9 wherein said further fluorinated surfactants comprise perfluorinated polyether surfactants.

11. Aqueous composition according to claim 1 wherein said aqueous composition comprises fluoropolymer particles.

12. Aqueous composition according to claim 11 wherein said fluoropolymer particles have an average diameter of 40 to 400 nm.

13. Aqueous composition according to claim 11 wherein the amount of fluoropolymer particles is between 15 and 70% by weight.

14. Aqueous composition according to claim 11 further comprising a non-ionic non-fluorinated surfactant.

15. Aqueous dispersion according to claim 14 wherein said non-ionic non-fluorinated surfactant corresponds to the formula:

$$R^1\text{—O—}[CH_2CH_2O]_n\text{—}[R^2O]_m\text{—}R^3 \qquad (XI)$$

wherein $R^1$ represents an aromatic or linear or branched aliphatic hydrocarbon group having at least 8 carbon atoms, $R^2$ represents an alkylene having 3 carbon atoms, $R^3$ represents hydrogen or a $C_1$-$C_3$ alkyl group, n has a value of 0 to 40, m has a value of 0 to 40 and the sum of n+m being at least 2.

16. Method comprising applying an aqueous composition as defined claim 1 to a substrate.

\* \* \* \* \*

UNITED STATES PATENT AND TRADEMARK OFFICE
CERTIFICATE OF CORRECTION

PATENT NO. : 7,659,333 B2  Page 1 of 1
APPLICATION NO. : 11/562277
DATED : February 9, 2010
INVENTOR(S) : Hintzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 43 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,659,333 B2  Page 1 of 2
APPLICATION NO. : 11/562277
DATED : February 9, 2010
INVENTOR(S) : Klaus Hintzer It is certified that error appears in the above-identified patent and that said Letters Patent is hereby corrected as shown below:

On the Title Page, Item (75) (Inventors)
Line 2, delete "Neuoetting" and insert in place thereof -- Neuöetting --.

Line 5, delete "Neuoetting" and insert in place thereof -- Neuöetting --.

On the Title Page, Item (74) (Attorney, Agent or Firm)
Line 1, delete "Enrich;" and insert in place thereof -- Ehrich --.

On the Title Page, Item (56) page 2 (Other Publications)
Line 28, delete "Emulusion" and insert in place thereof -- Emulsion --.

Line 47, delete "Perfluorvinyl" and insert in place thereof -- Perfluorovinyl --.

Column 3
Line 25, delete "or3." and insert in place thereof -- or 3. --.

Column 5
Line 48, delete "CFH" and insert in place thereof -- CHF --.

Line 50, delete "CFH" and insert in place thereof -- CHF --.

Column 6
Line 25 (approx.), delete "alkoholates" and insert in place thereof -- alcoholates --.

Column 8
Line 18, delete "tert.-" and insert in place thereof -- tert- --.

Line 19, delete "tert.-" and insert in place thereof -- tert- --.

Line 20, delete "ammonium-alkali-" and insert in place thereof -- ammonium- alkali- --.

Signed and Sealed this

Fourteenth Day of December, 2010

David J. Kappos
*Director of the United States Patent and Trademark Office*

CERTIFICATE OF CORRECTION (continued)
U.S. Pat. No. 7,659,333 B2

Column 9

Line 21 (approx.), after "$Z\text{-}R_f\text{-}O\text{-}CX{=}CX_2$" insert -- , --.

Column 11

Line 3, delete "GENAPOL®080" and insert -- GENAPOL®X080 --.

Line 63, delete "Tetrahydrofurane," and insert in place thereof -- Tetrahydrofuran, --.

Column 12
Line 16, delete "CuSO4." and insert in place thereof -- $CuSO_4$. --.

Line 40, delete "CuSO4." and insert in place thereof -- $CuSO_4$. --.

Line 64, delete "CuSO4." and insert in place thereof -- $CuSO_4$. --.

Column 16
Line 9, in Claim 16, after "defined" insert -- in --.